United States Patent [19]
Roberts

[11] Patent Number: 4,835,147
[45] Date of Patent: May 30, 1989

[54] DEHYDROEPIANDROSTERONE THERAPY FOR AMELEORATION OF PROSTATE HYPERTROPHY AND SEXUAL DYSFUNCTION

[75] Inventor: Eugene Roberts, Monrovia, Calif.

[73] Assignee: City of Hope, Duarte, Calif.

[21] Appl. No.: 46,579

[22] Filed: May 6, 1987

[51] Int. Cl.⁴ .............................................. A61K 31/56
[52] U.S. Cl. .................................................... 514/178
[58] Field of Search .......................................... 514/178

[56] References Cited

U.S. PATENT DOCUMENTS

| | | | |
|---|---|---|---|
| 4,496,556 | 1/1985 | Orentreich | 514/178 |
| 4,518,595 | 5/1985 | Coleman et al. | 514/178 |
| 4,542,129 | 9/1985 | Orentreich | 514/178 |

OTHER PUBLICATIONS

The Merck Index, 10th ed. (1983), #7606 Prasterone.

Primary Examiner—Douglas W. Robinson
Assistant Examiner—Joseph A. Lipovsky
Attorney, Agent, or Firm—Edward S. Irons

[57] ABSTRACT

Dehydroepiandrosterone and acceptable salts thereof are utilized for sexual disfunction therapy.

9 Claims, No Drawings

DEHYDROEPIANDROSTERONE THERAPY FOR AMELEORATION OF PROSTATE HYPERTROPHY AND SEXUAL DYSFUNCTION

This invention relates to the administration of dehydroepiandrosterone (DHEA) and its therapeutically acceptable salts, including the sulfate (DHEA-S) to ameliorate the symptoms of prostatic hypertrophy, certain symptoms of menopause particularly those related to nervous system dysfunction, and of psychosexual dysfunction symptoms such as inhibited sexual desire, inhibited sexual excitement and inhibited orgasm. These benefits may result from modification by DHEA or DHEA-S of the testosterone-estrogen ratio in human subjects.

DETAILED DESCRIPTION OF THE INVENTION

The enlargement of the prostate that takes place in later years in adult males is generally coincident with decreases with age in the levels of DHEA and DHEA-S in the blood. Normal prostatic function appears to depend on the capability of testicular and prostatic tissue to provide an appropriate ratio of testosterone to estrogens. DHEA and DHEA-S are precursors of androgens, including testosterone which, in turn, are precursors for estrogens. See generally, Roberts, E., *Treatment Development Strategies for Alzheimer's Disease*, Mark Pauley Associates, Inc., pp. 188, et seq (1986).

As a result of the decrease with age of DHEA and DHEA-S serum levels, the capability of prostatic and testicular tissues to make testosterone is impaired. While acceptable levels of the male hormone may be maintained, the subsequent synthesis of estrogen from testosterone is decreased. The result is the presence of testosterone without the counterbalancing effects of appropriate amounts of estrogen.

It is a postulate of this invention that the abnormality observed in prostatic hypertrophy is consequent from this imbalance in testosterone estrogen ratio. Pursuant to one aspect of the invention, DHEA or a therapeutically acceptable salt thereof is administered to human males with decreased serum levels of DHEA or DHEA-S to preclude the occurrence of prostatic hypertrophy or prevent it from progressing once it has begun.

A number of menopausal symptoms, particularly those related to nervous system dysfunction, also may be attributable to an imbalance in the appropriate testosterone to estrogen ratio. It is known that DHEA and DHEA-S decrease in the blood at the same time that estrogens decrease in menopause. Pursuant to this invention, DHEA or a therapeutically acceptable salt thereof is administered to human females to correct the hormone imbalance, and thus ameliorate the emotional and neural problems of menopause.

Human sexual dysfunction refers to sexual drive (libido), sexual excitement and orgasm. Common organic causes of sexual dysfunction include disruption of genital sensor or motor nerves, hormonal imbalances, vascular disease, drug side effects and diabetes. Psychosexual dysfunctions have no apparent organic basis. Treatment is primarily a matter of behavior modification and counseling.

The sole presently known prior art pertaining specifically to the pharmacologic treatment of psychological aspects of sexual dysfunction is a report of the administration of bupropion hydrochloride in a controlled clinical trial involving some sixty (60) test subjects which resulted in increased sexual desire and heightened libido. See *Time,* May 4, 1987, p. 6. (The drug Wellbutrin referenced in the *Time* article is understood to be bupropion hydrochloride.) Administration of bupropion is reported to result in an increase in serum DHEA-S.

It is a further postulate of the invention that the administration of DHEA or a therapeutically acceptable salt thereof ameliorates sexual dysfunction by modification of neurochemical, specifically androgen (testosterone), estrogen balance or by correction of neurochemical imbalance in human subjects. Specifically, another aspect of this invention entails the administration of DHEA or a therapeutically acceptable salt thereof, e.g., DHEA-S to enhance sexual desire and performance and to ameliorate sexual dysfunction in human male and female subjects.

For all purposes of this invention, dosage of DHEA or a salt thereof to establish and maintain appropriate serum levels is within the skill of the art. For example, 90 to 300 mg per day administered in three 30 to 100 mg aliquots is appropriate. A 350 to 400 mg serum level is preferably established and maintained by periodic, e.g., daily, administration, for such time as may be indicated by patient response to the therapy. Administration may be accomplished in any desired manner, e.g., orally, transdermally, by time lapse capsule, or intranasally.

DHEA or an acceptable salt thereof can be formulated into capsules, tablets, elixirs, or the like together with suitable excipients in a manner conventional in the art.

I claim:

1. A process for ameliorating symptoms selected from the group consisting of prostate hypertrophy symptoms and sexual dysfunction symptoms related to nervous system dysfunction which consists of administering an effective amount of dehydroepiandrosterone or a therapeutically effective salt thereof to a human manifesting such symptoms.

2. A process for the amelioration of the symptoms of prostatic hypertrophy which comprises administering an effective amount of dehydroepiandrosterone or a therapeutically acceptable salt thereof to a human male having such symptoms.

3. A process for ameliorating human psychosexual dysfunction which comprises administering a therapeutically effective amount of dehydroepiandrosterone or a pharmaceutically acceptable salt thereof to a human having such dysfunction.

4. The process of claim 3 in which the dysfunction is inhibited sexual excitement.

5. The process of claim 3 in which the dysfunction is inhibited libido.

6. The process of claim 3 in which the dysfunction is inhibited orgasm.

7. A process for enhancing human sexual excitement, libido and orgasm which comprises administering to a human an effective amount of dehydroepiandrosterone or a therapeutically acceptable salt thereof.

8. A process for ameliorating symptoms consequent from an imbalance in the testosterone-estrogen ratio in the serum of a human which comprises administering to said human an effective amount of dehydroepiandrosterone or a therapeutically effective salt thereof.

9. The process as defined by claim 8 which comprises administering to a human subject, whose serum contains a lesser amount thereof, an amount of dehydroepiandrosterone or dehydroepiandrosterone-S sufficient to establish and maintain in said subject a serum level of from about 350 mg to about 400 mg of dehydroepiandrosterone or dehydroepiandrosterone-S.

* * * * *